(12) United States Patent
Cohen et al.

(10) Patent No.: US 9,107,660 B2
(45) Date of Patent: Aug. 18, 2015

(54) WOUND CLOSURE DEVICE

(71) Applicant: Covidien LP, Mansfield, MA (US)

(72) Inventors: Matthew D. Cohen, Berlin, CT (US); Michael Primavera, Orange, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 13/738,360

(22) Filed: Jan. 10, 2013

(65) Prior Publication Data

US 2013/0197573 A1 Aug. 1, 2013

Related U.S. Application Data

(60) Provisional application No. 61/593,550, filed on Feb. 1, 2012.

(51) Int. Cl.
*A61B 17/04* (2006.01)
*A61B 17/06* (2006.01)

(52) U.S. Cl.
CPC ........... *A61B 17/06166* (2013.01); *A61B 17/04* (2013.01); *A61B 17/0487* (2013.01); *A61B 17/06* (2013.01); *A61B 2017/0608* (2013.01); *A61B 2017/06176* (2013.01)

(58) Field of Classification Search
CPC .... A61B 17/04; A61B 17/0487; A61B 17/06; A61B 17/06166; A61B 2017/0608; A61B 2017/06176
USPC .................. 606/139, 148–151, 157, 228–230
See application file for complete search history.

(56) References Cited

U.S. PATENT DOCUMENTS

| | | |
|---|---|---|
| 3,123,077 A | 3/1964 | Alcamo |
| 4,024,871 A | 5/1977 | Stephenson |
| 4,047,533 A | 9/1977 | Perciaccante et al. |
| 5,133,738 A | 7/1992 | Korthoff et al. |
| 5,226,912 A | 7/1993 | Kaplan et al. |
| 5,236,563 A | 8/1993 | Loh |
| 5,264,540 A | 11/1993 | Cooper et al. |
| 5,342,376 A | 8/1994 | Ruff |
| 5,569,302 A | 10/1996 | Proto et al. |
| 5,618,552 A | 4/1997 | Bezwada et al. |

(Continued)

FOREIGN PATENT DOCUMENTS

| | | |
|---|---|---|
| AU | 2006201924 A1 | 6/2006 |
| EP | 0 499 048 A1 | 8/1992 |

(Continued)

OTHER PUBLICATIONS

R.R. Szarmach et al., Journal of Long-Term Effects of Medical Implants, "An Innovative Surgical Suture and Needle Evaluation and Selection Program", JLT12(4), pp. 211-229 (175) (2002).

(Continued)

*Primary Examiner* — Ashley Fishback

(57) ABSTRACT

A wound closure device includes an elongated body with proximal and distal ends having a plurality of through-holes along the length and defining a longitudinal axis with a plurality of surface features extending away from the axis. The proximal end is configured and dimensioned to pass through body tissue and thereafter be selectively passed through at least one of the plurality of through-holes such that at least one of the surface features also passes through the through-hole thereby forming a locked closed loop to secure body tissue held therein.

12 Claims, 5 Drawing Sheets

(56) References Cited

U.S. PATENT DOCUMENTS

| | | |
|---|---|---|
| 5,683,417 A | 11/1997 | Cooper |
| 5,931,855 A | 8/1999 | Buncke |
| 6,063,105 A | 5/2000 | Totakura |
| 6,106,505 A | 8/2000 | Modak et al. |
| 6,143,352 A | 11/2000 | Clark et al. |
| 6,165,202 A | 12/2000 | Kokish et al. |
| 6,203,564 B1 | 3/2001 | Hutton et al. |
| 6,235,869 B1 | 5/2001 | Roby et al. |
| 6,241,747 B1 | 6/2001 | Ruff |
| 6,562,051 B1 | 5/2003 | Bolduc et al. |
| 6,599,310 B2 | 7/2003 | Leung et al. |
| 6,620,846 B1 | 9/2003 | Jonn et al. |
| 6,773,450 B2 | 8/2004 | Leung et al. |
| 2002/0077661 A1 | 6/2002 | Saadat |
| 2003/0074023 A1 | 4/2003 | Kaplan et al. |
| 2003/0149447 A1 | 8/2003 | Morency et al. |
| 2004/0010275 A1 | 1/2004 | Jacobs et al. |
| 2004/0030354 A1 | 2/2004 | Leung et al. |
| 2004/0060409 A1 | 4/2004 | Leung et al. |
| 2004/0060410 A1 | 4/2004 | Leung et al. |
| 2004/0088003 A1 | 5/2004 | Leung et al. |
| 2004/0153125 A1 | 8/2004 | Roby |
| 2004/0162580 A1 | 8/2004 | Hain |
| 2004/0185029 A1 | 9/2004 | Tang |
| 2005/0033367 A1 | 2/2005 | Leung et al. |
| 2005/0038472 A1 | 2/2005 | Furst |
| 2005/0125034 A1 | 6/2005 | Cichocki |
| 2005/0267531 A1 | 12/2005 | Ruff et al. |
| 2006/0111734 A1 | 5/2006 | Kaplan et al. |
| 2006/0188545 A1 | 8/2006 | Hadba |
| 2007/0005110 A1 | 1/2007 | Collier et al. |
| 2007/0038249 A1 | 2/2007 | Kolster |
| 2007/0142846 A1 | 6/2007 | Catanese et al. |
| 2007/0224237 A1 | 9/2007 | Hwang et al. |
| 2008/0058869 A1 | 3/2008 | Stopek et al. |
| 2008/0132943 A1 * | 6/2008 | Maiorino et al. ............. 606/228 |
| 2009/0099597 A1 * | 4/2009 | Isse ................................ 606/228 |
| 2009/0287245 A1 | 11/2009 | Ostrovsky et al. |
| 2009/0312791 A1 | 12/2009 | Lindh, Sr. et al. |
| 2010/0198257 A1 | 8/2010 | Stopek et al. |

FOREIGN PATENT DOCUMENTS

| | | |
|---|---|---|
| EP | 0 647 452 A1 | 4/1995 |
| EP | 1929961 A2 | 6/2008 |
| EP | 2108319 A1 | 10/2009 |
| EP | 2133028 A2 | 12/2009 |
| GB | 2337934 A | 12/1999 |
| GB | 2365351 A | 2/2002 |
| WO | 9620647 A1 | 7/1996 |
| WO | 9622735 A1 | 8/1996 |
| WO | WO 98/00065 | 1/1998 |
| WO | WO 98/52473 | 11/1998 |
| WO | WO 00/57933 A1 | 10/2000 |
| WO | WO 03/001979 A2 | 1/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/066927 | 8/2004 |
| WO | WO 2007/089864 | 8/2007 |
| WO | WO 2008/042992 | 4/2008 |
| WO | WO 2008/045376 A2 | 4/2008 |

OTHER PUBLICATIONS

George Odian, "Principles of Polymerization", III Edition, pp. 569-573 (1991).
Xu et al., "Towards Developing Surface Eroding poly($\alpha$-hydroxyl acids)", Biomaterials 27 (2006) 3021-3030.
Domb et al., Handbook of Biodegradable Polymer, Feb. 4, 1998, CRC Press ed. 1, p. 12.
Chu, Chih-Chang et al., Wound Closure Biomaterial and Devices, 1996, Publisher: CRC Press, Edition 1; p. 149.
International Search Report for European Application EP 06 01 2688 dated Oct. 9, 2007.
European Search Report for EP 08250199.0-2108 dated Jun. 16, 2008 (8 pages).
European Search Report for EP 10177651.6-1526 date of completion is Dec. 14, 2010 (3 pages).
European Search Report for European Application No. 10250002.2 dated Mar. 24, 2010. (9 pages).
International search Report from Application EP 06 01 2688 mailed Aug. 1, 2007.
International Search Report from the corresponding EP Appl. No. 13153553.6 dated Aug. 12, 2013.
International Search Report from EP Application No. EP 13153494.3 mailed May 3, 2013.

* cited by examiner

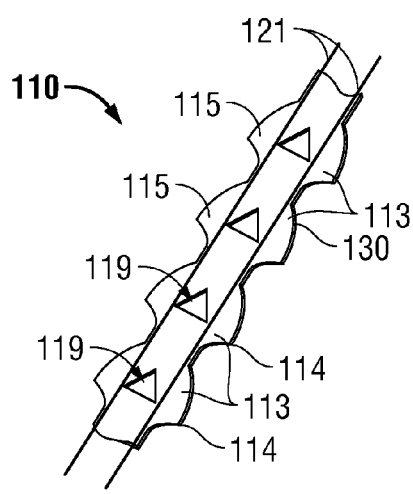
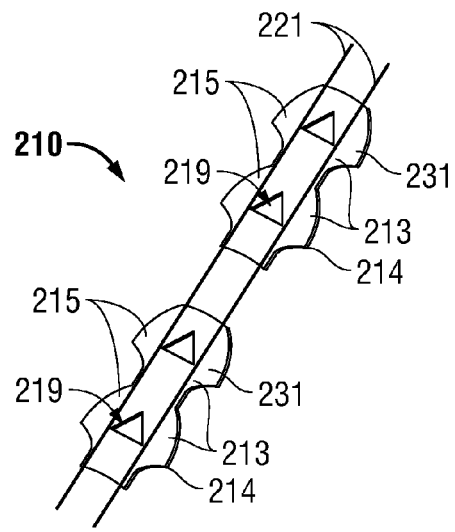
FIG. 3  FIG. 4
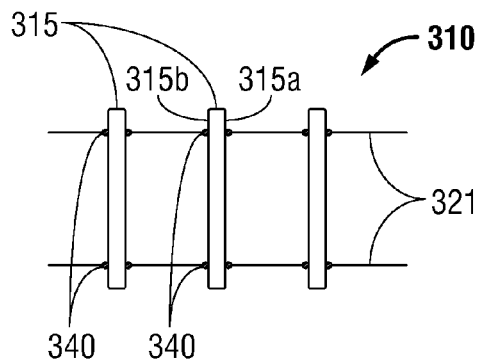
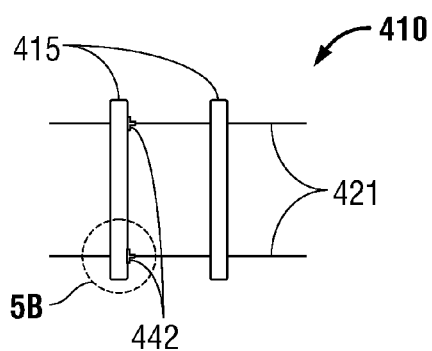
FIG. 5  FIG. 6A
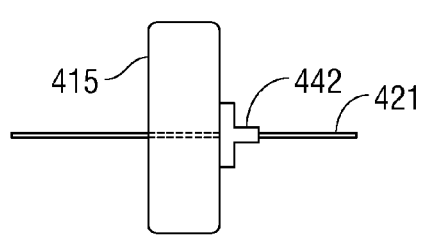
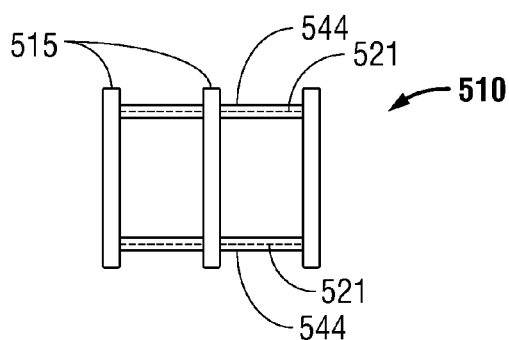
FIG. 6B  FIG. 7

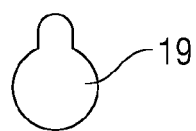 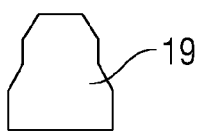 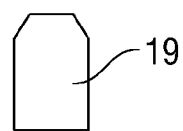
FIG. 8A  FIG. 8B  FIG. 8C
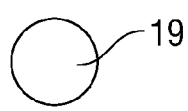 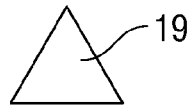
FIG. 8D  FIG. 8E
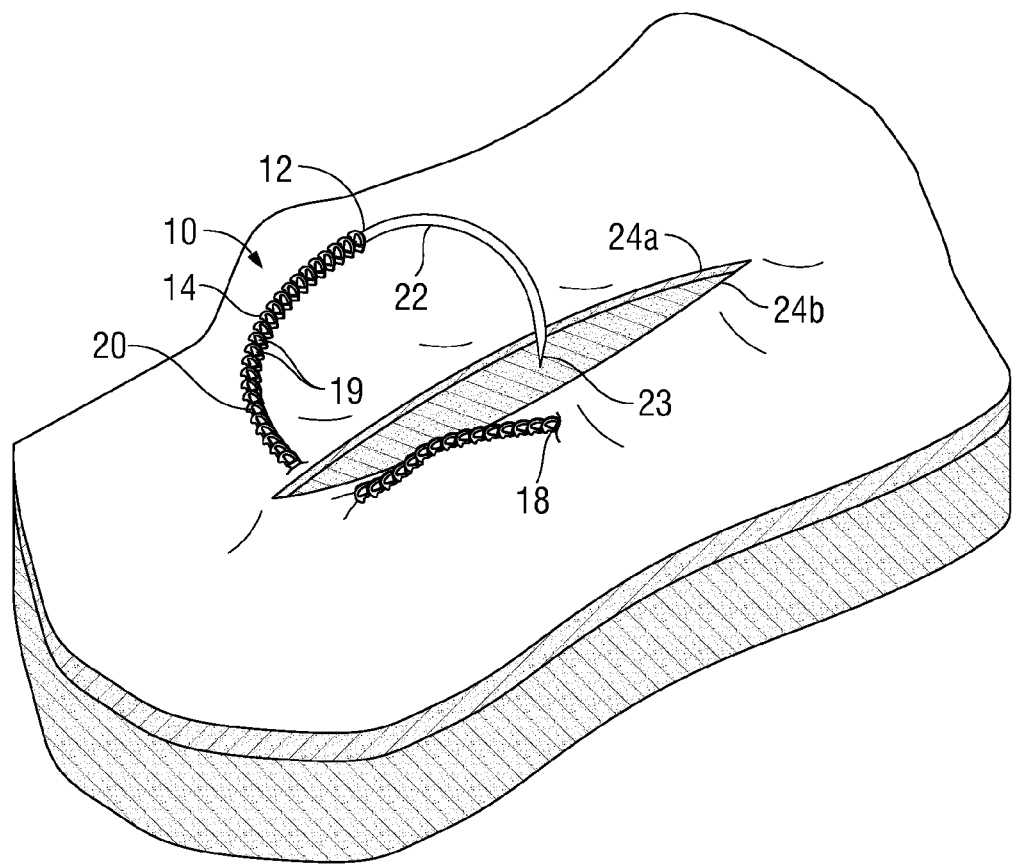
FIG. 9

WOUND CLOSURE DEVICE

CROSS-REFERENCE TO RELATED APPLICATIONS

This application claims the benefit of and priority to U.S. Provisional Patent Application No. 61/593,550, filed Feb. 1, 2012, the entire disclosure of which is incorporated by reference herein.

TECHNICAL FIELD

The present disclosure generally relates to wound closure devices having an uninterrupted or continuous stitch.

BACKGROUND OF RELATED ART

Suturing is a surgical technique involving the connection of tissue by stitching the tissue together with a strand of appropriate material. Suturing often involves piercing a needle with a suture attached thereto through tissue on both sides of a wound, pulling the ends of the suture to bring the sides of the wound together, and tying the suture into a knot. The knot preserves the tension on the suture to maintain the sides of the wound in approximation and allow the tissue to heal. An improperly tied knot can slip and untie at a tension far lower than the tension required to break the suture. When the suture is internal to the body, replacement of a failed suture can require additional surgeries.

A variety of devices have been developed for the transcutaneous placement, tying, and tightening of suture knots through a tissue tract. Despite the skill and due care involved in placing, tying, and tightening a suture knot using these devices, seepage of blood and fluids at the suture site and into the tissue tract can still occur.

Thus, improved systems and methods to achieve wound closures, which are substantially free of blood or fluid leakage about the wound closure site remain desirable.

SUMMARY

The present disclosure is directed to a wound closure device having an elongated body having a proximal end and a distal end, the elongated body including a plurality of segments having a plurality of preformed through-holes and a plurality of surface features extending generally outward from a longitudinal axis defined by the elongated flexible body; and at least one fiber disposed therethrough the plurality of segments, wherein the proximal end is configured and dimensioned to pass through body tissue and thereafter be selectively passed through at least one preformed through-hole, such that at least one of the plurality of surface features also passes through at least one preformed through-hole.

The present disclosure also includes a wound closure device comprising a plurality of segments defining an elongated flexible body having a proximal end and a distal end, wherein each of the plurality of segments comprises: at least one surface feature extending generally away from a longitudinal axis defined by the elongated flexible body; and at least one through-hole formed therethrough; and at least one fiber interconnecting the plurality of segments; wherein the proximal end is configured and dimensioned to pass through body tissue and thereafter be selectively passed through the at least one through-hole, such that the at least one surface feature also passes through the at least one through-hole.

The wound closure devices may include surface features which are configured to lock with at least one preformed through-hole, forming a locked closed loop. Certain embodiments include a plurality of surface features which enables movement of the device through tissue in a first direction and limits movement of the device in a second, opposite direction.

At least a portion of the plurality of segments may be spatially separated from each other or may be combined to form a substrate. Alternately, the plurality of segments be configured to couple to one another. Movement of the plurality of segments may be restricted along the fiber.

In certain embodiments, the wound closure device may include two fibers.

A method of closing a wound comprising wound closure devices of the present disclosure is described herein.

BRIEF DESCRIPTION OF THE DRAWINGS

Various embodiments of the present disclosure will be described hereinbelow with reference to the Figures wherein:

FIG. 3 is an enlarged view of a portion of an alternate embodiment of the wound closure device according to the present disclosure;

FIG. 4 is an enlarged view of a portion of yet an alternate embodiment of the wound closure device according to the present disclosure;

FIG. 5 is an enlarged view of a portion of another embodiment of the wound closure device according to the present disclosure;

FIG. 6A is an enlarged view of a portion of another embodiment of the wound closure device according to the present disclosure;

FIG. 6B is an enlarged view of the wound closure device of FIG. 5A according to the present disclosure;

FIG. 7 is an enlarged view of a portion of a separate embodiment of the wound closure device according to the present disclosure;

FIGS. 8A-E are top plan views of various embodiments of the plurality of through-holes of the device of FIG. 1; and FIGS. 9-12 illustrate a series of steps employing a method of closing a wound in accordance with the present disclosure.

DETAILED DESCRIPTION

The present disclosure provides for wound closure devices configured to form either uninterrupted or continuous stitches. The terms "uninterrupted" and "continuous" as used herein denote a single wound closure device being used to make two or more stitches. The wound closure device includes a plurality of segments, each of the segments including one or more surface features disposed on an outer periphery thereof and one or more openings defined within the segment. In embodiments, some of the segments may include only surface features, whereas some of the other segments include only the openings. The surface features are configured to interface with the openings of the segments. In embodiments, the openings may have a shape that is uniquely configured to match the surface features, allowing the surface features to pass through the openings and interlock therewith, thereby acting as a unidirectional locking mechanism. The surface features interlace through the openings and are secured therein via a frictional fit after tension is applied to the wound closure device.

The wound closure device of the present disclosure may be utilized with various wound closure techniques and tissue connection procedures, including, but not limited to, endoscopic techniques, plastic and reconstructive surgeries, general wound closure, cardiovascular, orthopedics, obstetrics, gynecology and urology, and combinations thereof. Suitable tissue types include, but are not limited to, various layers of muscle, ligaments, tendons, fascia, fat, skin, combinations thereof, and the like.

Figure 1:
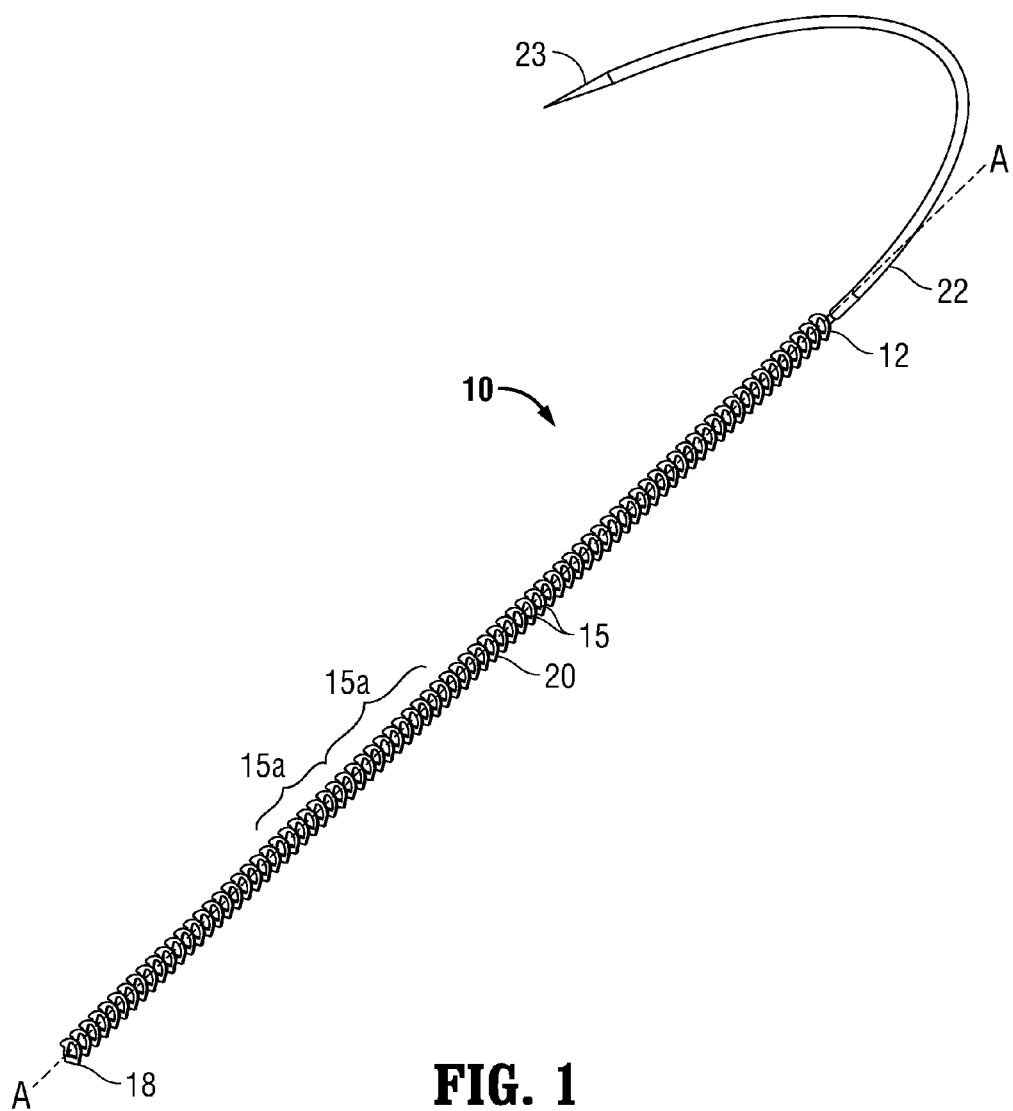
FIG. 1 is a perspective view of a wound closure device according to the present disclosure, the device possessing a plurality of through-holes.

Referring now in detail to the drawings in which like reference numerals are applied to like elements in the various views, a wound closure device 10 is shown in FIG. 1. The wound closure device 10 includes a flexible elongated body 20 defining a longitudinal axis A-A, the elongated body having a first end 12 attached to a needle 22 and a second end 18. In embodiments, the second end 18 may also be attached to a needle (not shown). The needle 22 includes a sharpened tip 23 which is configured and dimensioned to pass through body tissue.

Figure 2:
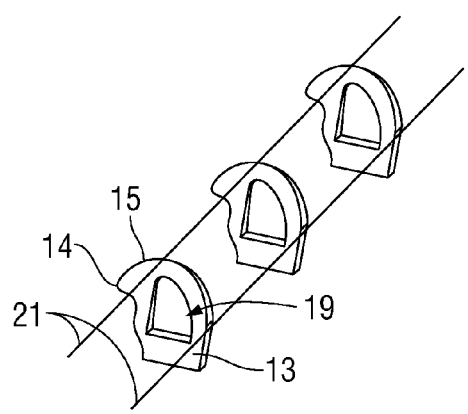
FIG. 2 is an enlarged view of a portion of the wound closure device of FIG. 1.

The flexible body 20 includes a plurality of segments 15. As shown in FIG. 2, each of the segments 15 includes a body 13 defining one or more surface features 14 and one or more preformed through-holes 19 therethrough.

With reference to FIGS. 1 and 2, the device 10 may also include one or more fibers 21 interconnecting the segments 15 along the longitudinal axis A-A. As shown in FIG. 2, the segments 15 are separated from each other and are interconnected via the fibers 21. The segments 15 may be loosely disposed or attached thereon the fibers 21 or may be secured thereto. Alternatively, the fibers 21 may be at least partially embedded in the segments 15 using any suitable technique where molten material (e.g., polymer) is formed around the fibers 21. In general, the fibers 21 extend the entire length of the elongated body 20 from the proximal end 12 to the distal end 18.

The fibers 21 reinforce the device 10 by providing additional structural support to the segments 15. As previously described, the fibers interconnect the segments, and may provide spatial separation between the segments. The fibers may be stitched therethrough the segments, enabling the segments to slidingly engage the fibers. Alternatively, the segments may be fixedly disposed on fibers via methods including overmolding, or the use of adhesives.

In other embodiments illustrated in FIG. 3, each of the segments 115 may be integrally formed with at least one neighboring segment 115 to form a continuous substrate 130, such as a chain or a ribbon, linking the plurality of segments 115. Two fibers 121 reinforce the segments 115. The fibers 121 run therethough the segments 115 and are enclosed within the segments 115. At least one through-hole 119 is disposed within each segment 115. Although a triangular through-hole 119 is illustrated, other shapes and geometries of through-holes are envisioned and described herein.

FIG. 4 illustrates another embodiment of a wound closure device 210, in which at least two segments 215 are joined together, creating a unit 231. Fibers 221 are disposed therethrough the units 231 and interconnect the units 231. The fibers 221 enable spatial separation from one unit 231 to the neighboring unit 231. As illustrated in FIG. 4, the units 231 are slidably disposed on the fibers 221. Movement of the units 231 across the fibers in not limited, that is, the units 231 may freely move laterally across the fibers 221. Methods for restricting lateral movement of segments and units will be described below. At least one through-hole 219 is disposed within each segment 115, and two through-holes 219 are disposed within each unit 231. Although a triangular through-hole 219 is illustrated, other shapes and geometries of through-holes are envisioned and described herein. Further, although two through-holes are illustrated, it is envisioned that each unit 231 may have one or more through-holes 219.

With reference to FIGS. 5-7, other embodiments of a wound closure device are shown in which movement of the segments or units along the fibers is restricted or limited. It should be understood the embodiments and methods described herein below may be used or combined with other embodiments described herein. For example, bumpers, knots, and spacers may be utilized with various embodiments described herein to restrict movement of segments and units.

Embodiments shown in FIGS. 5-7 illustrate methods for restricting movement of segments along the fibers in at least one direction. For example, FIG. 5 illustrates a wound closure device 310 having knots 340 disposed on each side 315a, 315b, of the segment 315 to secure and/or restrict lateral movement of the segment 315 along the fiber 321. The knots 340 may be disposed a predetermined distance or length along the fiber 321, allowing the segment 315 to travel along a predetermined length of the fibers 321 delineated by the knots 340. In further embodiments, the knots 440 may be disposed along a single side of the segments 415 preventing movement of the segments 315 along the fibers 321 only in a single direction (e.g., distally).

The knots 340 may be formed by tying knots at specified locations or lengths of the fiber 321. For ease of manufacturing, the fiber 321 may be tied in a knot 340, in between or after each segment 315 is inserted on the fiber 321. In other embodiments, a separate filament or fiber may used to tie a knot thereon the fiber 321. FIGS. 6A and 6B show another embodiment of a wound closure device 410 utilizing bumpers 442. Although the bumpers 442 are illustrated on one side of the segment 415, the bumpers 442 may be disposed on both sides of the segment 415. Further, the bumpers 442 may be disposed in between each segment 415 or alternatively, the bumpers 442 may be disposed at specified locations along the fiber 421. Alternately, bumpers 442 may be disposed only along one fiber 421, enabling flexing or bending of the segment relative to the fiber 421. That is, by having the bumpers 442 disposed on one side of the segment 415, the segment 415 is free to bend such that the segment 415 may be oriented horizontal in relation to the fiber 421, flattening out the wound closure device, facilitating tissue insertion.

It should be noted that FIG. 6B is similar to FIG. 6A, however FIG. 6B illustrates one fiber 421 running therethough the segment 415.

Bumpers 442 may be formed from the same or different materials as the fibers 421 or segments 415. In certain embodiments, the bumpers 442 may be secured to the fibers 421 via an adhesive or other suitable technique.

FIG. 7 shows yet another embodiment of the wound closure device 510. The wound closure device 510 includes a plurality of spacers 544, each of which is disposed about the fibers 521 between the segments 515. The spacers 544 may be loosely or slidably disposed on the fibers 521 or may be secured thereto via overmolding, stitching, adhesive, and combinations thereof. The spacers 544 may of different or same lengths and evenly space apart the segments 515. In addition, the spacers 544 also spatially separate segments 515 at a predetermined distance along the length of the fibers 521.

Wound closure devices of the present disclosure include a plurality of through-holes. The through-holes are flexible and may be compressible or expandable such that a needle and subsequent segments or in some embodiments, units, may be inserted therethrough. The cross-sectional geometry of the through-holes may vary to accommodate different needles and tissue types, providing different holding strengths. As shown in FIGS. 8A-E, the cross-sectional geometry of the plurality of through-holes 19 may include a key-shape as shown in FIG. 8A, a compound wedge as shown in FIG. 8, a wedge as shown in FIG. 8C, a circle as shown in FIG. 8D and a triangle as shown in FIG. 8E. The surface features 14 may include barbs, hooks, latches, protrusions, leaves, teeth, and combinations thereof.

As described herein, the surface features 14 may be aligned in a single direction to allow the elongated body 20 of the wound closure device 10 to move through tissue in one direction and resist moving through tissue in the opposite direction. As shown in FIG. 1, the surface features 14 on elongated body 20 may be formed into a single directional wound closure device 10. The surface features 14 permit movement of device 10 through tissue in the direction of movement of the sharpened tip 23 of needle 22 but are generally rigid in an opposite direction to prevent movement of device 10 in an opposite direction.

In alternate embodiments, wound closure devices may comprise a bi-directional device, having a needle disposed at both ends of the device. That is, the surface features may be aligned such that a first length of the device can move through tissue in a first direction and resist moving through tissue in the opposite direction, while a second length of the device can move through tissue in a second direction and resist moving through tissue in the opposite direction. With the exception of surface features aligned in two directions, it is envisioned that this device wound operate in the same manner. Mainly, a first needle and a first plurality of segments/units are passed through tissue and therethrough a first through-hole and a second needle and a second plurality of segments/units are passed through tissue and therethrough a second through-hole.

The surface features 14 may be arranged in any suitable pattern. The number, configuration, spacing and dimensions of the surface features 14 may also be varied based on the tissue in which the wound closure device is intended to be used. In repairing a wound in skin or tendon, the surface features 14 may be made relatively short and more rigid to facilitate entry into this rather firm tissue. In repairing fatty and relatively soft tissue, the surface features 14 may be made longer and spaced apart further to allow the wound closure device 10 to grip the tissue. Larger surface features may also be used for joining fatty and relatively soft tissues, whereas smaller surface features 14 may be more suitable for collagen-dense tissues.

In embodiments, when repairing tissue with multiple layers of different tissue types, a combination of large and small surface features 14 within the same structure may be used. Use of a combination of large and small surface features 14 within the same wound closure device 10 provides for maximum anchoring properties.

The surface features may be formed, in embodiments, by making acute angular cuts directly into the segments, with cut portions pushed outwardly and separated from the body to form the surface features 14. Cutting may be performed using a cutting bed, a cutting bed vise, a cutting template, and/or a blade assembly. In operation, the cutting device may be configured to produce a plurality of axially spaced surface features in the same or at a random configuration, and at different angles in relation to each other. In alternate embodiments, the surface features may be formed using any suitable technique including, but not limited to, injection molding, molding, milling, machining using lasers, machining using mechanical cutters, machining using water jets, and combinations thereof.

The segments, units, and substrates may be constructed from tapes, slit sheets, ribbons, and combinations thereof. The segments, including the surface features and the through-holes, may be formed using any suitable technique including, but not limited to, injection molding, molding, milling, machining using lasers, machining using mechanical cutters, machining using water jets, and combinations thereof.

Filaments forming the fibers and the segments may be formed using any technique within the purview of those skilled in the art, such as, for example, extrusion, molding and the like. In embodiments, the fibers and the segments can be extruded through an extruder unit of a conventional type, such as those disclosed in U.S. Pat. Nos. 6,063,105; 6,203,564; and 6,235,869, the entire disclosures of each of which are incorporated by reference herein.

The fibers may be formed from one or more filaments (e.g., monofilament or multifilament) and include, but are not limited to, braids, yarns, and combinations thereof. The fibers may be formed using any known technique including, but not limited to, braiding, weaving and/or knitting. The filaments may also be combined to produce non-woven fibers. The filaments may be drawn, oriented, crinkled, twisted, and/or commingled as part of the forming process.

As used herein, the term "yarn" denotes a plurality of filaments and the term "braid" denotes a plurality of yarns. The yarns may be either heterogeneous or homogeneous. As used herein, the term "heterogeneous yarn" denotes a configuration containing at least two dissimilar filaments mechanically bundled together to form a yarn. The filaments are continuous and discrete so, therefore, each filament extends substantially along the entire length of the yarn and maintains its individual integrity during yarn preparation, processing and use. As used herein, the term "homogeneous yarn" denotes a configuration containing substantially similar filaments. The filaments are also continuous and discrete. Therefore each filament extends substantially along the entire length of the yarn and maintains its individual integrity during yarn preparation, processing and use. The yarns may be further used to form heterogeneous or homogenous braids.

Referring now to FIGS. 8-12, a series of steps for closing a wound using the wound closure device 10 described above is shown. It should be understood that alternate embodiments of the wound closure devices described herein are used in a similar manner. In use, surface features 14 are inserted therethrough through one or more through-holes 19 penetrating through the longitudinal axis of the elongated body 20 of the device 10 and securing the segments 15 through a friction fit. Thus, as tension is applied to the device, a wedging action occurs thereby providing a more secure locking mechanism. The wound closure device 10 and method of closing the wound is intended for general wound closure and can be utilized as either an "uninterrupted" or "continuous" stitch.

In FIG. 9, the tip 23 of the needle 22 of wound closure device 10 is shown having penetrated both wound edges 24a, 24b, and approaching at least one of the plurality of through-holes 19 of wound closure device 10.

Figure 10:
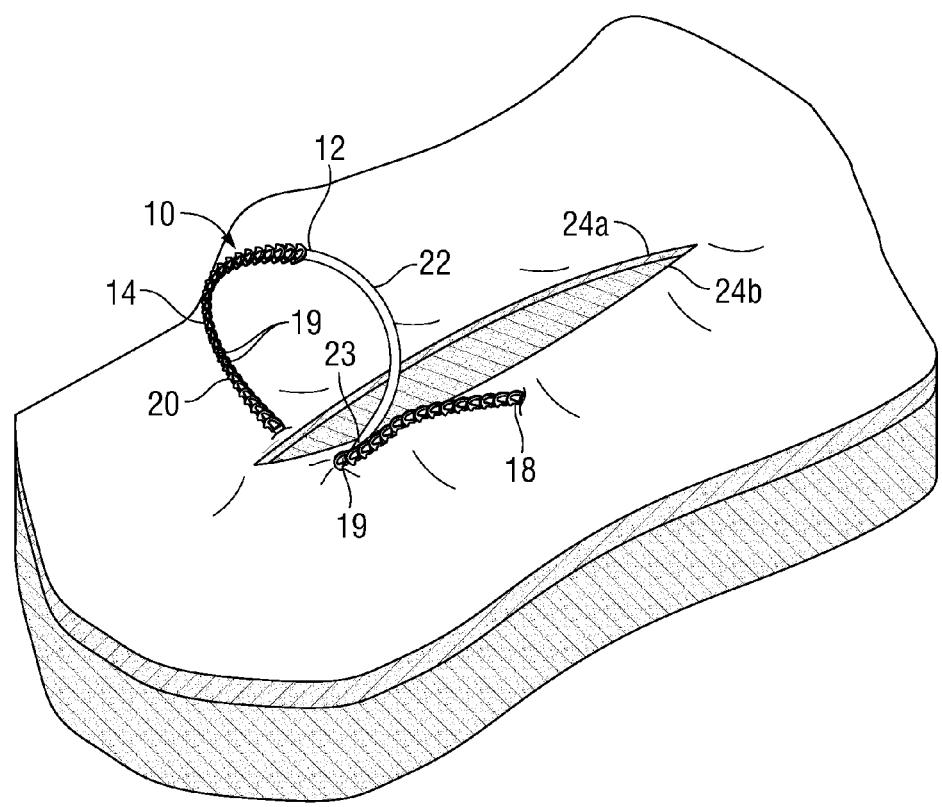
Figure 11:
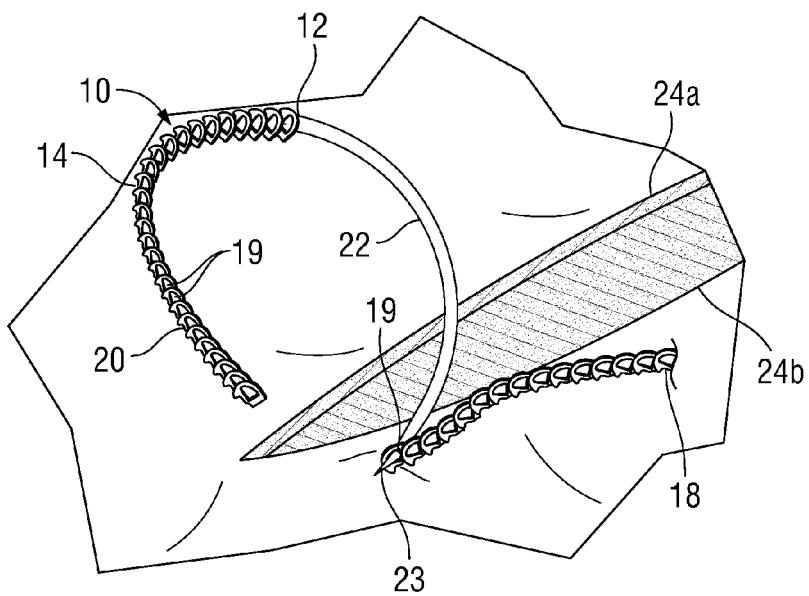
Figure 12:
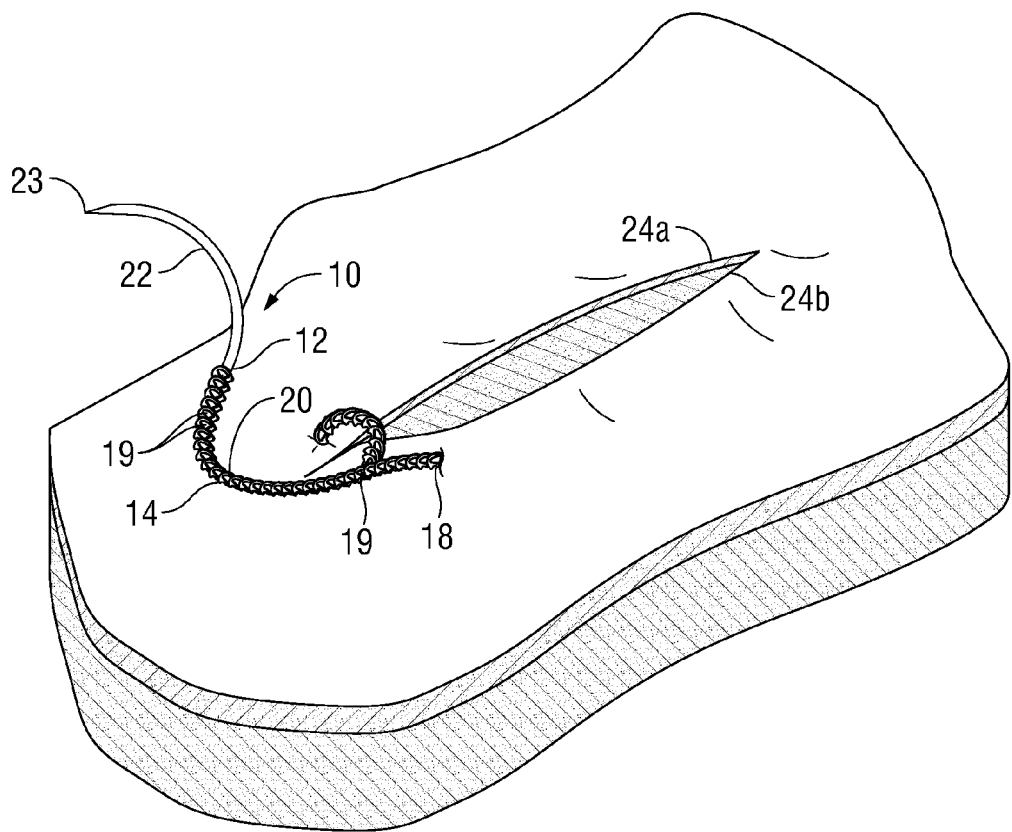

In FIG. 10-11, the tip 23 is shown penetrating through the through-hole 19. As proximal end 12 penetrates fully through the through-hole 19 and the suture is pulled through the through-hole 19. The surface features 14 may be compressed as they pass through the through-hole 19 of wound closure device 10 and expand upon exiting the other side of through-hole 19, thereby preventing reversal of the suture back through the through-hole 19. Additionally, the cross sectional dimension of flexible body 20 and the diameter of through-hole 19 may be formed so as to create a friction fit between the two, thereby securing device 10 through a friction fit as shown in FIG. 12.

The wound closure device may be formed from any suitable material including both biodegradable and non-biodegradable materials. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. It should be understood that such materials include natural, synthetic, bioabsorbable, and/or non-absorbable materials, as well as combinations thereof.

Suitable materials generally include polymers, metals and metal alloys, each of which may be biodegradable and non-biodegradable.

Wound closure devices in accordance with the present disclosure may be coated or impregnated with one or more medically useful substances, e.g., bioactive agents, which accelerate or beneficially modify the healing process when the device is applied to a wound or surgical site. Suitable bioactive agents include, for example, biocidal agents, antibiotics, antimicrobial agents, medicants, growth factors, anticlotting agents, analgesics, anesthetics, anti-inflammatory agents, wound repair agents and combinations thereof. Bioactive agents may be applied onto the wound closure device of the present disclosure utilizing any method within the purview of one skilled in the art including, for example, dipping, spraying, vapor deposition, brushing, compounding and combinations thereof.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A wound closure device comprising:
    a plurality of segments in spaced relation to each other, each segment of the plurality of segments having:
        a preformed through-hole; and
        a surface feature extending generally outward from a longitudinal axis defined through the plurality of segments; and
    at least one fiber passing through each of the plurality of segments such that the plurality of segments are movable along the at least one fiber, wherein at least one of the surface features is configured and dimensioned to pass through body tissue and thereafter be selectively passed through at least one of the preformed through-holes.

2. The wound closure device according to claim 1, wherein at least one of the surface features is configured to lock with at least one of the preformed through-holes thereby forming a locked closed loop.

3. The wound closure device according to claim 1, wherein the at least one fiber includes two fibers.

4. The wound closure device according to claim 1, wherein the surface features enable movement of the device through tissue in a first direction and limit movement of the device in a second, opposite direction.

5. The wound closure device according to claim 1, wherein the preformed through-holes have a shape complementary to a shape of the surface features.

6. A method of closing a wound comprising:
    providing a wound closure device in accordance with claim 1;
    passing the at least one surface feature of the wound closure device through body tissue at least once, and subsequently passing the at least one surface feature through at least one of the preformed through-holes, thereby forming a locked closed loop to secure body tissue held therein.

7. The method of closing a wound according to claim 6, wherein the passing step is repeated so that the at least one surface feature is passed through body tissue a plurality of times before the at least one surface feature is passed through the at least one of the preformed through-holes, thereby forming an uninterrupted stitch.

8. A wound closure device comprising:
    at least one fiber; and
    a plurality of segments disposed on the at least one fiber in spaced relation to each other, the at least one fiber passing through each of the plurality of segments such that the plurality of segments are movable along the at least one fiber, each of the plurality of segments including:
        at least one surface feature extending generally away from a longitudinal axis defined through the plurality of segments; and
        at least one through-hole formed therethrough;
    wherein the at least one surface feature is configured and dimensioned to pass through body tissue and thereafter be selectively passed through the at least one through-hole.

9. The wound closure device according to claim 8, wherein at least one of the surface features is configured to lock with the at least one of the preformed through-holes thereby forming a locked closed loop.

10. The wound closure device according to claim 8, wherein the at least one preformed through-hole has a shape complementary to a shape of the at least one surface feature.

11. A wound closure device, comprising:
    at least one fiber;
    a plurality of segments disposed on the at least one fiber in spaced relation to each other, the at least one fiber passing through each of the plurality of segments such that the plurality of segments are movable along the at least one fiber, each segment of the plurality of segments having:
        a body defining a preformed through-hole; and
        a surface feature extending outward from the body;
    wherein at least one of the bodies is configured and dimensioned to pass through body tissue and thereafter be selectively passed through at least one preformed through-hole, such that at least one of the surface features also passes through the at least one preformed through-hole.

12. The wound closure device according to claim 11, wherein the preformed through-holes have a shape complementary to a shape of the surface features.

* * * * *